Figure 2:
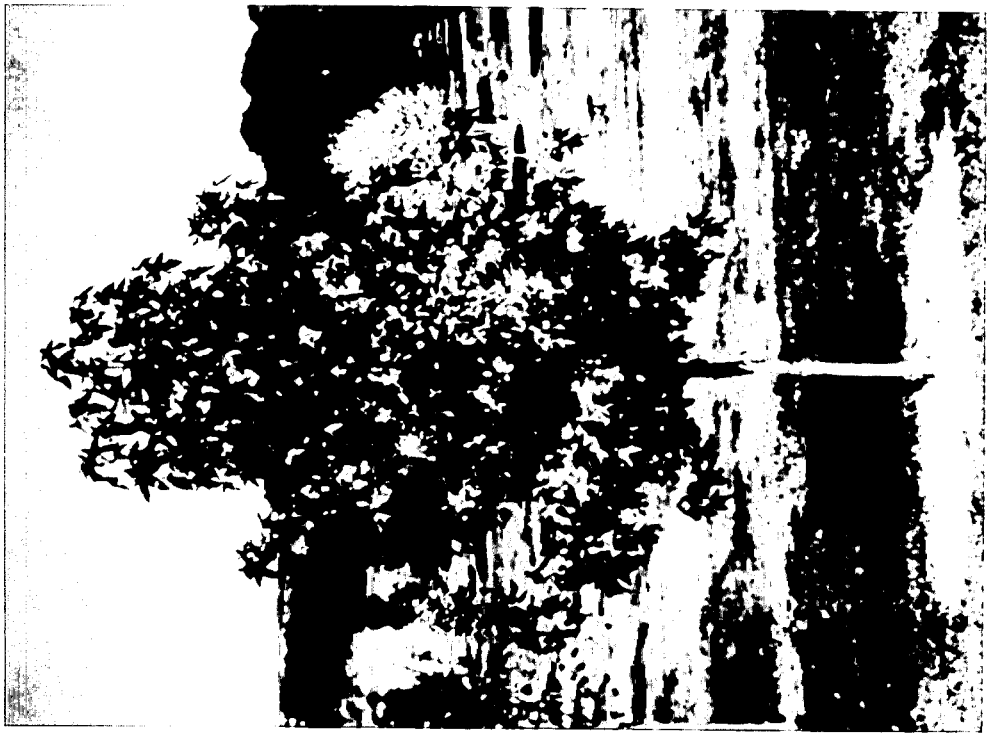

United States Patent [19]

Siebenthaler

[11] Plant 4,601

[45] Oct. 14, 1980

[54] SWEET GUM

[75] Inventor: John D. Siebenthaler, Dayton, Ohio

[73] Assignee: The Siebenthaler Company, Dayton, Ohio

[21] Appl. No.: 936,410

[22] Filed: Aug. 21, 1978

[51] Int. Cl.[3] ..... A01H 5/00

[52] U.S. Cl. ..... Plt./51

[58] Field of Search ..... Plt./51

[56] References Cited

PUBLICATIONS

Bailey, L. H., "Liquidambar", *The Standard Cyclopedia of Horticulture,* The MacMillian Co., N.Y., 1935, p. 120, (from vol. II).

Larrimer, W. H. et al., "Trees and Homes", *Trees the Yearbook of Agriculture,* 1949, U.S. Department of Agriculture, U.S. Government Printing Office, Wash., D.C., pp. 53, 54, 61, 62, 79.

*Primary Examiner*—Robert E. Bagwill
*Assistant Examiner*—James R. Feyrer
*Attorney, Agent, or Firm*—Biebel, French & Nauman

[57] ABSTRACT

A sweet gum having an unusual coloration during the fall season including on the same tree at any given time multi-colored leaves of purplish blue, red, orange, pink and yellow, of various hues, with the coloration lasting longer than is normal for the species.

3 Drawing Figures

1

The present invention relates to a new and distinct variety of *Liquidamber styraciflua,* commonly called sweet gum. I discovered my new variety of seedling mutation among a group of nursery plants of the *Liquidamber styraciflua* species which were being grown in a cultivated nursery in Dayton, Ohio. The tree of the present invention was asexually reproduced at my direction in the aforementioned nursery by both budding and grafting.

The distinctive features of the tree of the present invention are characterized in that it exhibits a green foliage throughout the summer turning in autumn to a myriad of colors including a progression of color change throughout the tree, although not simultaneously and all leaves do not progress through the complete change, from green to yellow to orange to pink to red and then purplish blue. Unlike the present tree, the species tree usually exhibits a much more uniform color change in the autumn throughout the tree which progresses from green to yellow and then to bronze or dark red or scarlet, and does not present the deep purplish blue color as occurs in some of the leaf color change of the present tree. Also, since the leaf color change in the present tree is much less uniform and is random throughout the tree, it appears as a multi-colored tree rather than a single colored tree as is typical of the species. Also, the fall coloration of the present tree begins earlier, typically two or three weeks, and remains for a longer time than is typical of the species. For example, the tree of the present invention has been seen to maintain its fall coloration for at least 30 days, whereas it is common for the species to only retain full coloration for approximately 2 to 3 weeks. A further distinctive characteristic is exhibited by a superior hardiness to survive cold through the winter including temperatures in excess of −21° F. without exhibiting any bud or branch damage. This was particularly notable in comparison to seedlings of the general species in the same nursery which showed damage or total kill into 2–3 year wood or killing of the tree completely.

Figure 1:
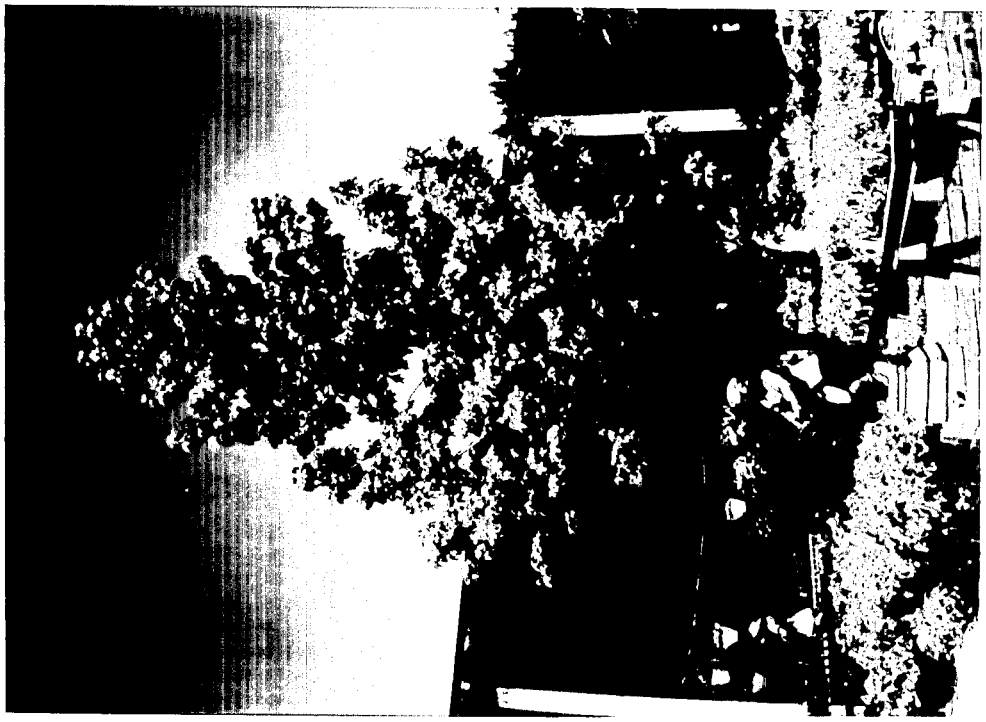

FIG. 1 is a color photograph taken in approximately the early summer, of a young fully formed specimen of a tree of the present invention;

2

Figure 3:
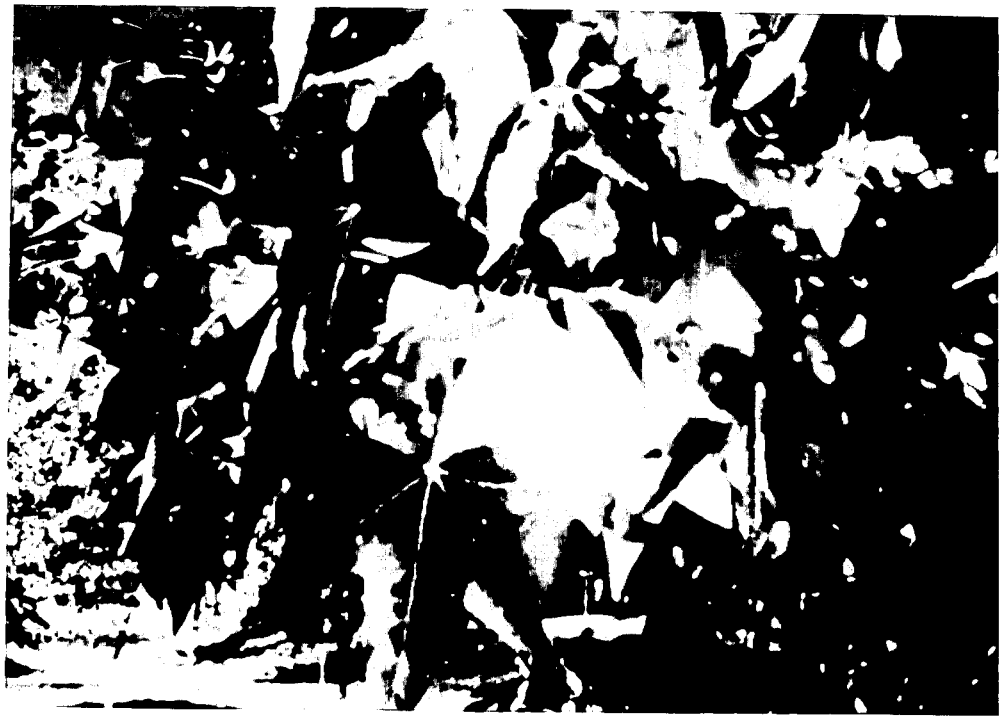

FIG. 2 is a color photograph taken in the fall, of another young fully formed specimen of a tree of the present invention showing the unusual fall coloring; and FIG. 3 is a close-up color photograph taken in the fall, of the leaves on a tree of the present invention, showing some of the variety of colors of the leaves.

The following is a detailed description of my new variety of sweet gum, with color terminology in accordance with the "Royal Horticultural Society Color Chart," published by the Royal Horticultural Society in London. It is pointed out, however, that the coloration of leaves as indicated below are only approximate because the color variation is considerable as the leaves age. In addition, the size of the leaves vary from tree to tree and depend to some extent on the growing season.

Parentage: A seedling mutation of unknown parentage.

Propagation: Holds distinguishing characteristics through succeeding propagation by budding and grafting.

Locality where grown and observed: Dayton, Ohio.

Tree: Upright, symmetrically cone-shaped, healthy and extremely hardy.

Branches: Normal amount of cork.

Foliage: 5–7 lobed (7 lobes are only occasionally observed) with acuminate, finely serrate lobes, lustrous and dark green above, paler below, glabrous above and below except large tuffs of pale rufous hairs in the axils of the principal veins; typically 3–7 inches across with petioles 5–7 inches long; color-Willow green 000862/1 through most of the season, some remaining that color in the fall and others having various hues on the same leaf, as mentioned above, being a blend of Tangerine orange 9/3 and Currant red 821/2, Jasper red 018/2, Yellow ocra 17-07/3, Claret rose 021/2, Purplish blue Bcc39, Greenish maroon 1030/3 and dark Wisteria blue 640 as well as many other hues and shades.

I claim:

1. A new and distinctive variety of *Liquidamber styraciflua* substantially as herein shown and described characterized particularly in the extent to which the multitude of fall colors are developed randomly throughout the tree and substained and in the hardiness of the tree to survive colder temperatures.

* * * * *